United States Patent [19]

Labno et al.

[11] Patent Number: 5,267,282
[45] Date of Patent: Nov. 30, 1993

[54] DEVICE FOR MONITORING THE STACK EXIT AIR IN A REACTOR INSTALLATION

[75] Inventors: Leszek Labno, Nussbaumen; Claus-Detlef Schegk, Klingnau, both of Switzerland

[73] Assignee: Asea Brown Boveri Ltd., Baden, Switzerland

[21] Appl. No.: 913,055

[22] Filed: Jul. 14, 1992

[30] Foreign Application Priority Data

Jul. 18, 1991 [CH] Switzerland ............... 02152/91

[51] Int. Cl.⁵ ............................................. G21C 19/42
[52] U.S. Cl. .................................. 376/313; 376/310; 376/309
[58] Field of Search ............... 376/313, 310, 309, 316, 376/283, 293, 256; 976/DIG. 207, DIG. 172; 261/DIG. 10, 5, DIG. 54; 250/364, 380

[56] References Cited

U.S. PATENT DOCUMENTS

| | | | |
|---|---|---|---|
| 3,459,635 | 8/1969 | Bevilacqua et al. | 376/313 |
| 4,092,541 | 5/1978 | Neidl | 250/364 |
| 4,663,113 | 5/1987 | Jester et al. | 376/256 |
| 4,859,405 | 8/1989 | Squarer et al. | 376/299 |
| 4,863,677 | 9/1989 | Eckardt | 376/313 |
| 4,927,596 | 5/1990 | Minnick | 376/283 |

FOREIGN PATENT DOCUMENTS

3637845 5/1988 Fed. Rep. of Germany .

OTHER PUBLICATIONS

Patent Abstracts of Japan—vol. 13, No. 200 (P-869)(3548) May 1989.
Patent Abstracts of Japan—vol. 1, No. 128 (M-043) Oct. 1977.
Patent Abstracts of Japan—vol. 8, No. 223 (P-307)(1660) Oct. 1984.
Patent Abstracts of Japan—vol. 14, No. 44 (P-996)(3987) Jan. 1990.
Patent Abstracts of Japan—vol. 3, No. 155 (E-160) Dec. 1979.
Patent Abstracts of Japan—vol. 13, No. 185 (P-865)(3533) May 1989.

*Primary Examiner*—Donald P. Walsh
*Assistant Examiner*—Meena Chelliah
*Attorney, Agent, or Firm*—Burns, Doane, Swecker & Mathis

[57] ABSTRACT

A device for monitoring the stack exit air in a reactor installation consists essentially of a pressure relief line (2) which connects the containment vessel (1) to the stack (5) and in which a filter unit (3) is located. Downstream of the filter, a sampling point (6) is provided in the pressure relief line, from where gas mixture is branched off via a sampling line (7). This gas is passed through a measurement section (14) and then returned into the pressure relief line (2). The concentration of the gas is reduced in a dilution unit (8) upstream of the measurement section (14). Cooling of the gas sample in the sampling line (7) before dilution is prevented by means of a heater (24).

3 Claims, 1 Drawing Sheet

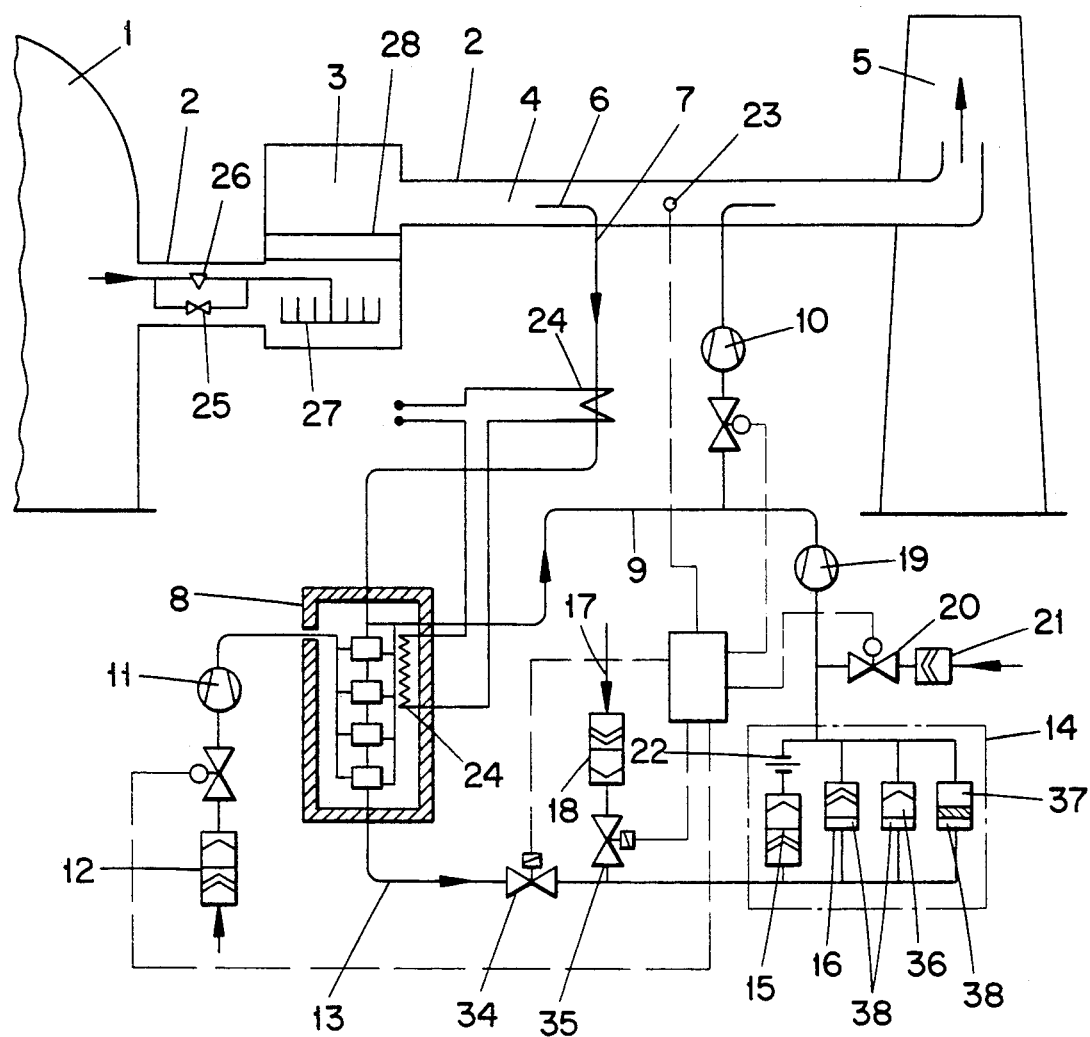
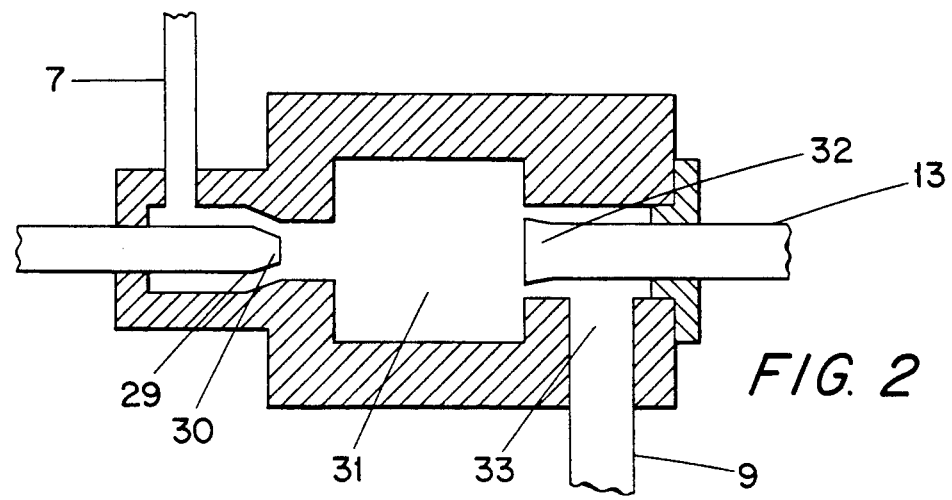

ic patent 5,267,282

DEVICE FOR MONITORING THE STACK EXIT AIR IN A REACTOR INSTALLATION

BACKGROUND OF THE INVENTION

1. Field of the Invention

The invention relates to a device for monitoring the stack exit air in a reactor installation, essentially consisting of a pressure relief line which connects the containment vessel to the stack and in which a filter unit is located, a sampling point being provided downstream of the filter, from where gas mixture is branched off via a sampling line, passed through a measurement section and then returned to the stack exit air.

2. Discussion of Background

The atmosphere in the containment vessel of a nuclear power station consists as a rule of air, steam, hydrogen, $CO_2$, rare gases, iodine and aerosols. In normal operation of the installation, this mixture, which has an activity of about $10^3$ Bq/m$^3$, is discharged from the containment vessel via a venting unit directly into the stack. In the event of an accident with a small leakage in the primary system, during which the activity is between $10^3$ Bq/m$^3$ and $10^8$ Bq/m$^3$, the gas is likewise discharged via the venting unit directly into the stack. In the event of a major accident with, for example, core meltdown, the activity can become greater than $10^{14}$ Bq/m$^3$. During a major accident, the venting unit is isolated, whereupon the pressure in the containment vessel rises. To avoid an unduly great pressure rise, the containment vessel is relieved via a filter unit. In this filter unit (for example a dry filter or wet filter), the activity of iodine and aerosols is reduced by a factor of at least 1,000. Downstream of the filter unit, the activity of the gas is then determined in a measurement section.

Because of the remaining very high activity in the downstream pure-gas line leading to the stack, the measuring apparatus used for normal operation, such as balancing filters and aerosol monitors cannot be used, since the measuring range would be exceeded and handling of the balancing filter would not be ensured. For this reason, special instruments having a wider measuring range and involved screenings as well as complicated devices for handling the balancing filter are normally used.

SUMMARY OF THE INVENTION

The invention attempts to avoid these disadvantages. Accordingly, one object of this invention is to provide, in an installation of the type described at the outset, for operation of the installation with the existing measuring instruments and apparatus even in the event of an accident.

According to the invention, this is achieved when the activity concentration of the gas is reduced in a dilution unit upstream of the measurement section.

The advantages of the invention are to be seen, inter alia, in the elimination of the hitherto usual heavy screenings around the entire measurement section. Screening for the transport of the balancing filter to be measured is also eliminated, whereby the hazard for the operating personnel is greatly reduced.

It is particularly advantageous, if the gas sample in the sampling line is protected from cooling by means of a heater, before it is diluted. This avoids, on the one hand, condensation of steam in the sampling line and measurement section and an associated erroneous measurement due to precipitation of iodine and aerosols.

BRIEF DESCRIPTION OF THE DRAWING

A more complete appreciation of the invention and many of the attendant advantages thereof will be readily obtained as the same becomes better understood by reference to the following detailed description when considered in connection with the accompanying drawings of an exemplary embodiment of the invention relating to the exit air side part of a pressurized water reactor installation, wherein:

FIG. 1 shows a simplified diagram of an exit air side part of a reactor installation, and FIG. 2 shows a basic sketch of a dilution stage.

Only the elements essential for understanding the invention are shown. For example, the entire primary and secondary sections of the reactor installation are not shown. The directions of flow of the working media are indicated by arrows.

DESCRIPTION OF THE PREFERRED EMBODIMENTS

Referring now to the drawings, wherein like reference numerals designate identical or corresponding parts throughout the several views, the containment vessel of the reactor is marked 1 in FIG. 1. A pressure relief line 2, the first part of which is called raw gas line below, leads from the containment vessel to the filter unit 3. A control valve 25 and a bursting disk 26 for defined pressure relief are located in two parallel planes in the raw gas line. A throughput measurement, which is not shown, likewise takes place in the raw gas line. In the case of the example, the filter unit operates according to the wet-filter principle; the type of filter is irrelevant to the use of the invention. In Venturi internals 27, the water is atomized and thus purifies the gases. The purified gases then flow through a water separator 28. They then enter the second part of the pressure relief line 2, called pure gas line 4 below, which leads to the stack 5.

In the pure gas line 4, a sampling point 6 is provided, from which a gas sample is continuously taken and introduced into a sampling line 7. The sampling could also be carried out from an exit air duct or exit air stack downstream of the junction of the pure gas line with such a duct or stack. As an example, it may be mentioned that about 10 m$^3$/h are branched off from a total exit gas rate of 20,000 m$^3$/h. This gas sample is heated by means of a heater 24, operated electrically or by heat exchange, over preferably the entire length of the sampling line 7, in order to avoid condensation.

From the sampling line, a part stream is passed to the dilution unit 8. This unit designed as a plurality of stages operates with a defined volumetric flow of particle-free compressed air. This is made available by a compressor 11, upstream of which an iodine filter and an aerosol filter 12 are provided. In principle, only the first two stages of the plurality of dilution stages are heated, since the temperature can no longer fall below the dewpoint after the second stage, even in the case of pure steam in the pure gas line 4.

A dilution stage shown in FIG. 2 functions as follows: the compressed air provided flows through an annular gap 29 around the suction nozzle 30 for the gas mixture which is to be diluted. Due to the resulting reduced pressure, the aerosol is drawn in at a certain volumetric flow and mixed homogeneously with the pure air in the mixing chamber 31. If the pure air volumetric flow is increased, the flow velocity in the annular gap increases to the same extent. As a result, the reduced pressure at the suction nozzle increases, whereby the volumetric flow of the gas mixture also increases. Both volumetric flows are thus coupled by the reduced pressure and their ratio remains constant even for different upstream pressures.

In the dilution unit 8, a dilution of, for example $1:10^4$ is desired. It is of advantage here to accomplish the dilution in a plurality of cascades, which reduces the air requirement for clean dilution air. Only a part of the diluted sample, taken from the sampling line 7, is taken from the mixing chamber 31 and fed to the next stage. This part stream sampling takes place via the extraction nozzle 32. Care must be taken here that this sampling takes place under isokinetic conditions. These apply if the flow velocity in the nozzle 32 is equal to that in the flow channel at the point of extraction. Via various nozzle diameters, different volumetric extraction flows can be adapted to different total volumetric flows. This is of importance for the last stage. As an example, it may be assumed that only 0.3 $m^3/h$ from the total extraction rate of 10 $m^3/h$ indicated above are utilized for the measurement. After the dilution, however, a total of about 3 $m^3/h$ is fed to the measuring apparatus. The residual air of 7.8 $m^3/h$ for all dilution stages, remaining after the isokinetic part stream sampling, flows through the exit air branch 33 outwards into the return line 9 (FIG. 1). In this return line, the remainder of the sample air and the air from the exit air branches 33 are delivered by a pump 10 back into the pure gas line 4. With this return, care must be taken that no back-pressure, which might affect the dilution ratio, is generated in the mixing chamber of the dilution stage.

As a result of the dilution, the activity of the precipitated substances is reduced to a level which is also usual in normal operation. The handling and evaluation of the measuring apparatus can thus take place in the usual manner even in the event of an accident.

The measurement line 13 (FIG. 1) which leads to the actual measurement section 14 is connected to the extraction nozzle 32 of the last stage. This measurement section 14, provided also for normal operation of the installation and shown greatly simplified, consists, on the one hand, of a combination 15 of aerosol- and iodine-balancing filters for discontinuous measurement. For quasi-continuous monitoring, an aerosol monitor 16, an iodine monitor 36 and a rare gas monitor 37 are provided. These three monitors are each fitted with a radiation detector 38. The relative activity of the aerosols is detected by this mere indication. Furthermore, it defines the change intervals of the balancing filters.

In the normal operation, discontinuous measurement via the elements 15 is normally carried out once per week. In the event of an accident, however, it is envisaged that the measurement is carried out every 4 hours. For this purpose, the balancing filters are dismantled, transferred into a separate room and evaluated there by means of a spectrometer for specific nuclides.

Prior to the measurement, the measurement section 14 is flushed, so that the filter activity caused by the rare gas components is reduced to an irrelevant level and does not falsify the actual measurement. For this purpose, the measurement line 13 is isolated by means of a shut-off device 34, and the flushing air line 17 is opened by means of a shut-off device 35. Atmospheric air is drawn in via the transfer pump 19 and passes via iodine- and aerosol-filters 18 into the measurement section. The flushing air is expelled into the return line 9. Of course, it can also be discharged directly into the stack 5.

During the actual measurement, the flushing air line 17 is isolated by the shut-off device 35, and the measurement line 13 is opened by the shut-off device 34. The mixture to be measured is drawn in by the same transfer pump 19. Since this pump is designed for the higher flushing air rate, atmospheric air is also drawn in for control purposes in the case of measurement. For this purpose, there is a control valve 20 with an upstream aerosol filter 21 in a branch line upstream of the pump.

Upstream of the junction of the part measurement section having the aerosol monitor with that having the balancing filters, a flow rate meter 22 is located in the latter. The flow rate via the aerosol- and iodine-filters is measured therein and integrated over the dust introduction time. In this way, the activity concentration values are determined. To derive the activity relief rate, the concentration is correlated with the throughput measurement.

Even though, as mentioned above, the throughput is measured in the raw gas line, a correlation with this measurement would lead to erroneous results. This is because, during a pressure relief, the throughputs in the raw gas line and in the pure gas line can be very different particularly in the initial phase. This can, for example, be due to the steam content condensing out in the still cold water receiver of the filter unit 3. Consequently, the flow is determined once more at 23 in the pure gas line 4. This can be a Venturi measurement or a determination via a pressure/temperature measurement. The result is linked to the concentration values in order to determine the activity relief rates.

Obviously, numerous modifications and variations of the present invention are possible in the light of the above teachings. It is therefore to be understood that, within the scope of the appended claims, the invention may be practiced otherwise than as specifically described herein.

What is claimed as new and desired to be secured by Letters Patent of the United States is:

1. A device for monitoring the stack exit air in a reactor installation, essentially comprising:
    a pressure relief line which connects a containment vessel to a stack;
    a filter unit located in the pressure relief line;
    a sampling point provided in the pressure relief line downstream of the filter unit for taking a gas sample stream from the pressure relief line;
    a sampling line branching off the sampling point and connecting to the stack;
    a dilution unit interposed on the sampling line for diluting the gas sample with dilution air to reduce the activity concentration of the gas; and,
    a measurement section located downstream of the dilution unit for measuring the activity of the sample gas stream upstream of the measurement section.

2. The device as claimed in claim 1, wherein a heater, which prevents cooling of the gas sample before dilution, is provided in the sampling line.

3. The device as claimed in claim 1, wherein the dilution unit is provided with a plurality of stages.

* * * * *